United States Patent
Seshimoto et al.

(10) Patent No.: US 6,375,856 B1
(45) Date of Patent: *Apr. 23, 2002

(54) METHOD OF RECOVERING BLOOD FILTRATION RESIDUES

(75) Inventors: Osamu Seshimoto; Kenichiro Yazawa; Takaki Arai, all of Saitama (JP)

(73) Assignee: Fuju Photo Film Co., Ltd., Kanagawa (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/464,614

(22) Filed: Dec. 15, 1999

(30) Foreign Application Priority Data

Dec. 15, 1998 (JP) ............................... 10-355475

(51) Int. Cl.[7] ..................... B01D 29/62; B01D 41/00; B01D 61/14; B01D 65/02
(52) U.S. Cl. ................. 210/791; 210/483; 210/488; 210/650; 210/651; 210/767; 210/797; 210/798; 436/177
(58) Field of Search ................................ 210/650, 651, 210/767, 483, 488, 435, 791, 793, 797, 798; 436/177, 178

(56) References Cited

U.S. PATENT DOCUMENTS

| | | | | |
|---|---|---|---|---|
| 4,330,410 A | * | 5/1982 | Takenaka et al. | 210/767 |
| 4,416,777 A | * | 11/1983 | Kuroda et al. | 210/446 |
| 6,045,699 A | * | 4/2000 | Yazawa et al. | 210/637 |
| 6,120,474 A | * | 9/2000 | Okuda et al. | 604/4.01 |

* cited by examiner

Primary Examiner—John Kim
(74) Attorney, Agent, or Firm—Reed Smith LLP

(57) ABSTRACT

The invention provides a method of recovering filtration residues of blood which comprises filtering blood by a blood filtering device comprising a blood filtering material which is a depth filtering material and a holder which contains the blood filtering material and has a blood inlet and filtrate outlet, after finishing the filtering blood, feeding aqueous liquid to the filtrate outlet to recover the filtration residues accumulated in the blood filtering material.

3 Claims, 3 Drawing Sheets

METHOD OF RECOVERING BLOOD FILTRATION RESIDUES

BACKGROUND OF THE INVENTION

This invention relates to a method of recovering blood cell components from whole blood.

Blood analysis is roughly divided into the analysis of blood cell components and plasma components, and however, main analysis is carried out as to plasma components.

The analysis of blood cell components is divided into the analysis based on the outer shape of erythrocyte, leukocyte or the like and the analysis of contents. In the analysis based on the outer shape, for example, in the case of leukocyte, construction, size, normality or abnormality of form and the like of various types of leukocyte, such as cells in various growing stages from blast cells, granulocyte and lymphocyte are investigated. In the analysis of contents, DNA, hemoglobin content of erythrocyte and the like are analyzed. The analysis based on the outer shape are mostly carried out by the observation of whole blood through a microscope, but collection of blood cell components by centrifugation is also carried out. In the case of the analysis of contents, blood cells are collected by centrifugation, and then purified.

When the analysis based on the outer shape is carried out using whole blood, exact observation is difficult. Although the difficulty in observation can be solved by centrifuging it is possible to break the form of blood cells.

SUMMARY OF THE INVENTION

An object of the invention is to provide a method for preparing blood cell samples which are deformed little and can be observed easily by a simple means.

The inventors noted that, as the means for separating plasma sample for the analysis of blood cell components, centrifugation requires labor and time, and centrifugation is unsuitable particularly for treating a small number of samples rapidly and for the in site inspection because of requiring a centrifuge and electric power. Thereupon, they have been developing blood filter cartridges which separate plasma or serum from whole blood by filtration using depth filtering material. Japanese Patent KOKAI 9-196911, 9-276631, 10-185780, 10-185909, 10-227788, etc.

Through the development, they found that blood cell components accumulated in the depth filtering material after blood filtration are suitable as the sample for the analysis of blood components based on the outer shape and the like, and can be recovered without or with a small deformation by backwashing the depth filtering material. In the case of hemolyzing blood cells to measure blood cell components, interference of plasma proteins can be removed by washing erythrocytes.

Thus, the present invention provides a method of recovering filtration residues of blood which comprises filtering blood by a blood filtering device comprising a blood filtering material which is a depth filtering material and a holder which contains the blood filtering material and has a blood inlet and filtrate outlet, after finishing the filtering blood, feeding aqueous liquid from the filtrate outlet to recover the filtration residues accumulated in the blood filtering material.

It is also effective to remove proteins by washing blood cells prior to the backwaching.

Figure 1:
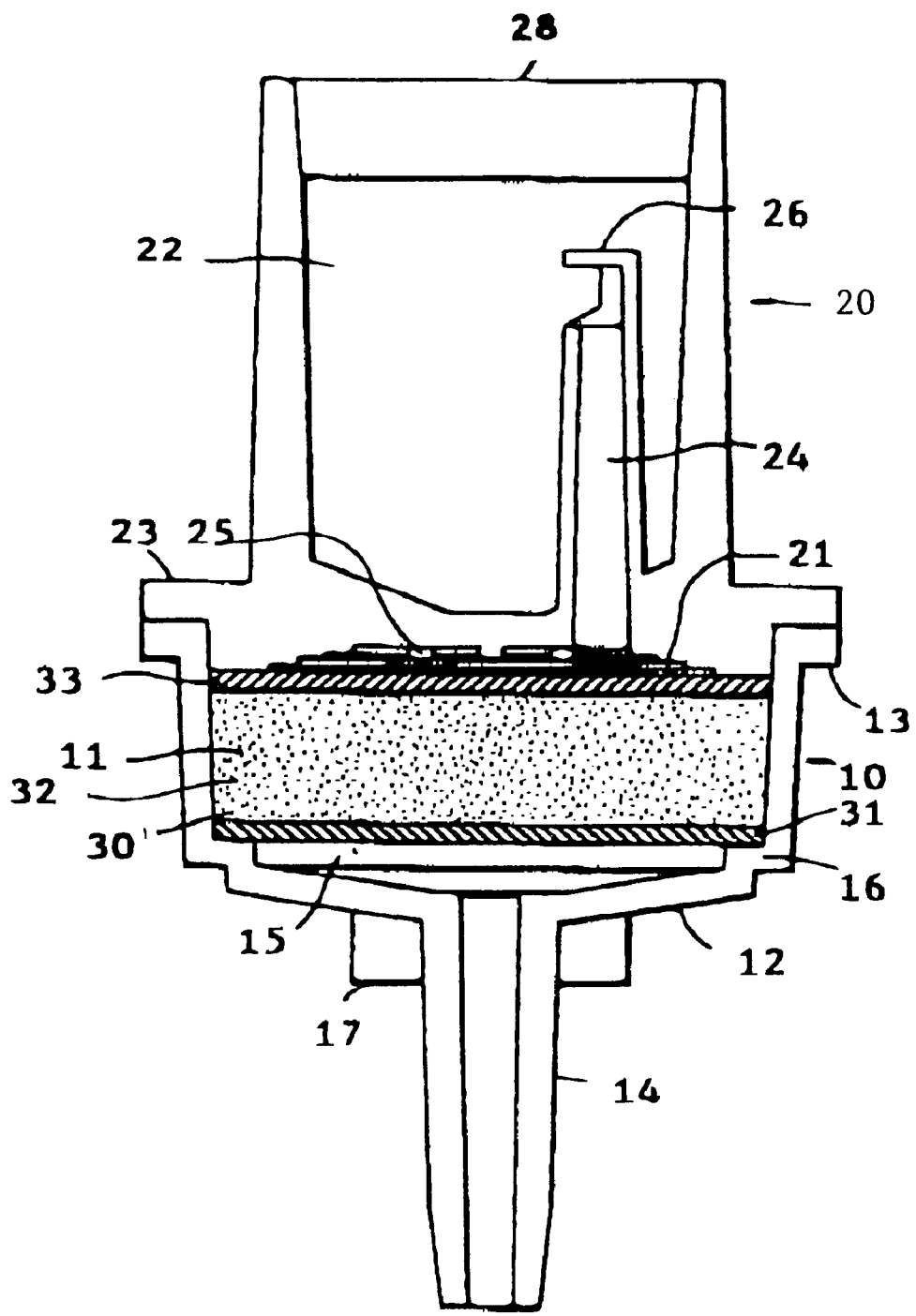
FIG. 1 is a longitudinal section of a blood filter cartridge used in the example.

10 . . . Holder body
11 . . . Filtering material chamber
12 . . . Disc portion
13 . . . Flange
14 . . . Blood inlet
15 . . . Space
16 . . . Spacer
17 . . . Flap
20 . . . Cap
21 . . . Step
22 . . . Plasma receiver
23 . . . Flange
24 . . . Plasma passage
25 . . . Projection (adhesion inhibiting means)
26 . . . Pent roof
27 . . . Partition wall
28 . . . Suction port
30 . . . Blood filtering material
31 . . . Nylon mesh
32 . . . Glass fiber filter flake layer
33 . . . Polysulfone porous membrane (microporous membrane)

DETAILED DESCRIPTION OF THE INVENTION

Although the type of the blood filtering material is not limited, in the filtering material of the invention, it is thought that the filter material to be used does not trap blood cells only by the surface, but catches to remove blood cells gradually by entangling at first large blood cell components and then smaller blood cell components in the space structure with permeating in the thickness direction in total of the filtering material, called the volumetric filtration or depth filtration. Preferable blood filtering material are glass fiber filter, and a combination of glass fiber filter and microporous membrane is particularly preferred.

Preferable glass fiber filter has a density of about 0.02 to 0.5 g/cm$^3$, preferably about 0.03 to 0.2 g/cm$^3$, more preferably about 0.05 to 0.13 g/cm$^3$, a retainable particle size of about 0.6 to 9 μm preferably 1 to 5 μm. By treating the surface of glass fiber with hydrophilic polymer as disclosed in Japanese Patent KOKAI Nos. 2-208676, 4-208856, filtration proceeds more fast and smoothly. Lectin or other reactive reagent or modifier may be incorporated into glass fiber, or glass fiber may be treated therewith. Two or more glass fiber filters may be superimposed.

It is also possible that a glass fiber filter sheet is cut into small pieces, and packed in a holder. The thickness of glass fiber filter sheet is about 0.2 to 3 mm, usually about 0.5 to 2 mm. The glass fiber filter sheet is cut into pieces having a diameter of about 10 to 30 mm, preferably about 15 to 25 mm. The shape of the piece is not limited, and may be square, rectangle, triangle disc or the like.

Microporous membranes having blood cell-separating ability of which the surface has been made hydrophilic separate whole blood into blood cells and plasma specifically without hemolysis to the degree of substantially influencing analytical values. A suitable pore size of the microporous membrane is smaller than the retaining particle size of glass fiber filter, and is 0.2 μm or more, preferably about 0.3 to 5 μm, more preferably about 0.5 to 3 μm. The void content of the microporous membrane is preferably higher, and a suitable void content is about 40 to 95%, preferably about 50 to 95%, more preferably about 70 to 95%. Illustrative of the microporous membranes are polysulfone membrane, fluorine-containing polymer membrane, etc.

Preferable microporous membranes are polysultone membrane, cellulose acetate membrane, and the like, and particularly preferred one is polysulfone membrane. In the blood filtering material of the invention, the glass fiber filter is located on the blood inlet side and the microporous membrane is located on the filtrate outlet side. The most preferable blood filtering material is a combination of the glass fiber filter or the aggregate of extra fine fibers and polysulfone membrane laminated in this order from the blood inlet side.

A suitable thickness of the glass fiber filter varies according to the plasma volume to be recovered and density (void content) and area of the glass fiber filter. A necessary amount of plasma for analyzing plural items using dry analytical elements is 100 to 500 $\mu$l. In practical viewpoint, a glass fiber filter having a density of about 0.02 to 0.2 g/cm$^3$ and an area of 1 to 5 cm$^2$ is suitable. In this case, a suitable thickness of the glass fiber filter layer is about 1 to 10 mm, preferably about 2 to 8 mm, more preferably about 4 to 6 mm. The above thickness can be made by superposing 2 to 10 sheets, preferably 3 to 8 sheets of glass fiber filter.

A suitable thickness of the microporous membrane is about 0.05 to 0.5 mm, preferably about 0.1 to 0.3 mm, and the number of the microporous membrane is usually one. However, two or more sheets of microporous membrane may be used, if necessary.

Respective layers may be integrated by joining each other using partially disposed (e.g. spots) adhesive, according to disclosures in Japanese Patent KOKAI Nos. 62-138756-8, 2-105043, 3-16651, etc.

The blood filtering material is placed in a holder having a blood inlet and a plasma outlet. The holder is, in general, formed of a body containing the blood filtering material and a cap, and each of them is provided with at least one aperture. One is used as the blood inlet, and the other is used as the filtrate outlet, optionally further as a suction port. A suction port may be provided separately. In the case that the holder is rectangular and is provided with the cap on a side of the holder, both of the blood inlet and the plasma outlet may be provided on the holder body.

The volume of the filter chamber which contains the blood filtering material is necessary to be greater than the total volume of the blood filtering material both in a dry state and in a swelled state upon absorbing a sample (whole blood). When the volume of the filter chamber is smaller than the total volume of the blood filtering material, filtration does not proceed efficiently and hemolysis occurs. A suitable ratio of the volume of the filter chamber to the total volume of the blood filtering material in a dry state is, in general, 101 to 200%, preferably 110 to 150%, more preferably 120 to 140%, although the ratio varies according to the swelling degree of the filtering material. An actual volume is set depending on the necessary amount of plasma or serum, and is about 0.5 to 2.5 ml, usually about 0.6 to 2 ml, especially about 0.7 to 1.5 ml.

Besides, it is preferable that the periphery of the blood filtering material is closely fitted to the wall of the filter chamber so as not to form a bypass of whole blood without passing the filtering material.

The suction nozzle for sucking blood is connected to the blood inlet of the holder. The nozzle may be integral with or separate from the holder. In the case of a separate body, the nozzle is fixed to the holder body, and the connecting portion has a closed structure. The connecting means may be adhesion, fusion, screwing, fitting or the like.

The blood filter cartridge is made into a closed structure except the blood inlet and the plasma outlet by attaching a cap to the holder body.

As the material of the holder, thermoplastic or thermosetting plastics are preferable. Illustrative of the plastics are general-purpose plystyrene, high impact polystyrene, methacrylate resin, polyethylene, polypropylene, polyester, nylon, polycarbonate, etc. The material may be transparent or opaque.

Fitting of the cap to the holder body may be any means, such as adhesion using adhesive or fusion welding. On that occasion, either periphery of the holder body or of the cap is located on the inside, or both peripheries are butted. The fitting may be in a state of detachable utilizing screws or the like.

The shape of the blood filtering material is not restricted, but disc and polygon is preferable in view of production. By rendering the size of the blood filtering material slightly greater than the inside section of the holder body (i.e. filter chamber), breakthrough of blood at the periphery of the filtering material can be prevented. To render the shape square is preferable because of no generation of cutting loss. Moreover, cut pieces of glass fiber filter can also be served.

Although the blood filtration using the above blood filter cartridge is not restricted, the pressure difference between the blood inlet and the filtrate outlet is preferably 200 mmHg or less, more preferably 170 mmHg or less, particularly preferably 150 mmHg or less, so as not to break blood cells. The lower end of the pressure difference is not restricted, and in the practical viewpoint of filtration time, 30 mmHg or more, preferably 50 mmHg or more is desirable.

In particularly preferable filtration, after feeding blood to be filtered, strictly after contacting the blood with glass fiber filter, the pressure difference between the blood inlet and the filtrate outlet is kept 50 mmHg or less at least for 5 seconds. A preferable pressure difference in the first step is 30 mmHg or less, and it is possible to spread blood naturally. A preferable keeping time is 10 seconds or more.

A suitable feeding volume of blood is about 1.2 to times, preferably 2 to 4 times the volume of blood filtering material, and in the case of glass fiber filter, about 1.2 to 3 times, preferably 1.2 to 2 times the volume of glass fiber filter.

After the above first step, blood filtration is accelerated by sucking from the filtrate outlet side and/or by pressurizing from the blood inlet side. A convenient sucking, pressurizing means is to use a peristaltic pump or syringe. The pressure difference is 200 mmHg or less at the maximum, and is preferably 170 mmHg or less, particularly preferably 150 mmHg or less. The lower end of the pressure difference is not restricted, and in the practical viewpoint of filtration time, 30 mmHg or more, preferably 50 mmHg or more is desirable. A preferable traveling length of the piston in the case of using a syringe is about 2 to 5 times the volume of the filtering material as the stroke volume. A suitable traveling speed of the piston is about 1 to 500 ml/min·cm$^2$, preferably about 20 to 100 ml/min·cm$^{2.}$ Incidentally, hematocrit value of blood greatly varies, and thereby, filtration resistance (elevation speed of pressure difference according to pressurizing or reducing pressure varies). That is, when pressure is increased or decreased at a constant speed, in the case of blood having a great hematocrit value, pressure difference rapidly increases to bring sharp decrease of filtration speed caused by clogging of filtering material or breakage of blood cells caused by the addition of great pressure difference prior to obtaining a desired amount of plasma or serum. On the other hand, in the case of blood having a small hematocrit value, filtration speed is too great, and leakage of blood cells occurs. Thereupon, it is preferable to suck and/or pressurize at a definite speed pattern after supplying blood to filtering material, to trace pressure difference variation between the blood inlet side and the filtrate outlet side with time, to estimate the hematocrit value of the filtering blood based on the detected pressure difference, and to adjust thereafter the suction and/or pressurizing speed. The above definite speed pattern is in general a constant speed, but any other definite speed pattern is also applicable. The adjustment of suction and/or pressurizing speed according to the hematocrit value is, in the case of high hematocrit value blood, to keep the variation rate of suction and/or pressurizing small and to lower the maximum pressure reduction rate (to lengthen the time for filtration), because hemolysis is liable to occur. In the case of low hematocrit value blood, the adjustment is to add relatively high suction and/or pressurizing speed, because hemolysis scarcely occurs and filtration is easily carried out.

An actual process is to determine an optimum pattern of suction pressure and suction period as to various whole blood samples different in hematocrit value. Since the hematocrit value of a blood sample to be filtered is not known, suction is started according to the suction pattern of a standard blood (e.g. hematocrit value: 45%), and the hematocrit value of the blood sample is estimated by the variation with time and the difference from the standard value. Then, filtration is continued, while the suction pressure an suction period are adjusted so as to meet the optimum pattern. This process is also applicable to the case of pressure filtration.

After the blood filtration is finished, separated plasma or serum is removed. Subsequently, the aqueous liquid for recovery is fed from the filtrate outlet side of the blood filtering device to wash out the blood cell components accumulated in the blood filtering material to recover them. Optionally, washing water is fed in the some direction as the blood filtration to wash the blood cell components accumulated in the blood filtering material prior to washing out of the blood cell components.

The aqueous liquid for recovery is pure water, physiological saline, various buffers, mad the like. A suitable volume of the aqueous liquid for recovery is about 0.5 to 10 times, preferably about 0.5 to 5 times the volume of blood filtering material.

It is possible that the blood filtering device is used as a preserving container for blood or the like by introducing the aqueous liquid for recovery into the blood filtering device, after the blood filtration is finished.

EXAMPLES

Example 1

(1) Preparation of Holder

Figure 2:
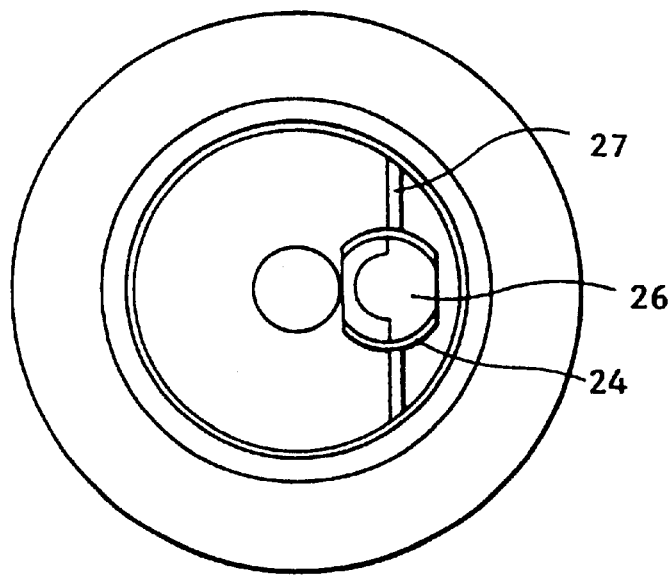
FIG. 2 is a plan view thereof.
Figure 3:
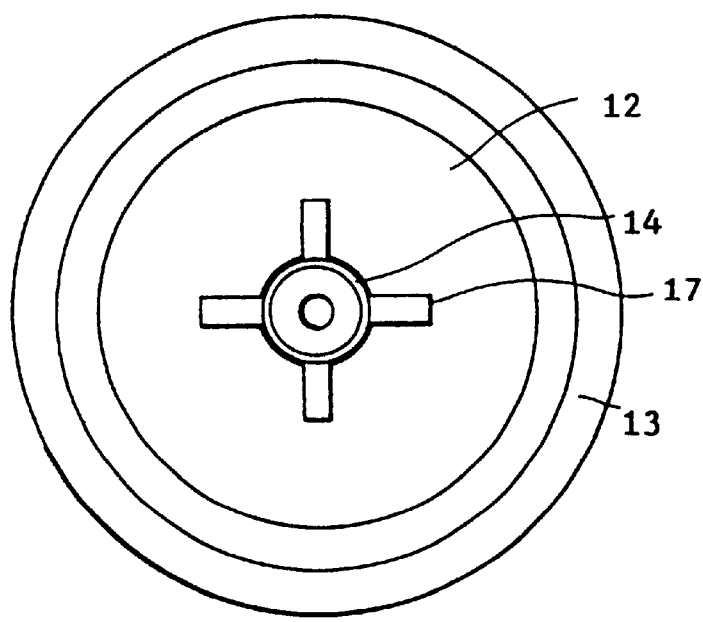
FIG. 3 is a bottom view of the holder body thereof.
Figure 4:
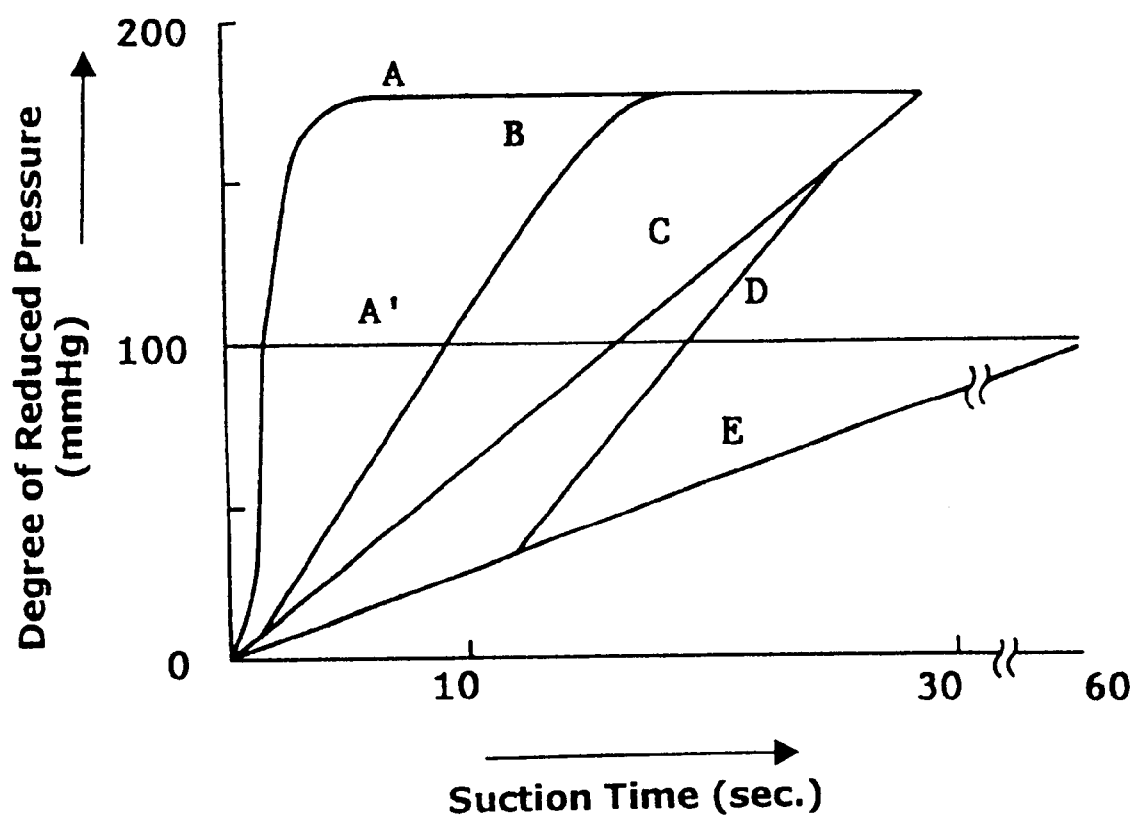
FIG. 4 is a graph illustrating various suction patters.

A blood filter unit illustrated in FIGS. 1–3 was prepared. The filter unit was composed of a holder body 10 and a cap 20, as shown in FIG. 1 which illustrates an assembled state of the filter unit.

The holder body 10 is formed of a filter chamber 11 (diameter:20.1 mm) for accommodating blood filtering material(s) 30 and a flange 13 formed outward at the upper end of the filter chamber 11. The bottom of the filter chamber 11 is made by a thin funnel-shaped circle plate portion 12 with a step portion near the periphery, and a nozzle-shaped blood inlet 14 is extended downward from the center of the circle plate portion 12. The above step portion functions as a spacer 16 for separating the underside of the blood filtering material 30 from the funnel-shaped circle plate portion 12 to form a space 15. As shown in FIGS. 1 and 3, flaps 17 are formed on the base portion of the blood inlet 14 toward four directions. The flaps 17 are for holding a sample tube (not illustrated) containing blood by fitting thereto.

The underside of the bottom of the cap 20 is recessed to form an upper space wherein 4 steps 21 are formed in a concentric circle shape. Five projection 25 are projected downward as the means for preventing adhesion in the central portion in the shape of 5 spots in a die. A plasma passage 24 in a smokestack-shaped with shaving in parallel stands upward from near the middle point between the center and periphery, and a pent-roof 26 which prevent spouting upward of discharged plasma is provided at the top of the plasma passage 24 in the horizontal direction. As shown in FIG. 2, the pent-roof 26 has a shape of a combination of two half circles. The half circle on the periphery side is in consistent with the outer wall of the plasma passage 24, and the half circle on the center side is in consistent with extension of the inner wall of the plasma passage 24. A partition wall 27 is formed in straight interposing the plasma passage in order to ensure a sufficient depth even in a small plasma volume. The upper end of the plasma receiver 22 is opened, and it becomes a suction port 28. A flange 23 is formed outward near the lower end of the cap 20, and the flange 23 is joined to the flange 13 of the holder body by ultrasonic welding. A rib (not illustrated) is formed on the face of the flange 23 facing the flange 13 of the holder body so as to ensure liquid-tight ability at the joined portion.

(2) Assembling of Filter Unit

Six sheets of glass fiber filter (GF/D, Whatman) punched into disc 20.3 mm in diameter were superposed and put in the holder body 10 (inside diameter:20.1 mm) made of plastic. A sheet of polysulfone microporous membrane 33 (SE-200, Fuji Photo Film Co., Ltd.) 170 $\mu$m in thickness punched into disc 20.7 mm in diameter was put thereon. The cap 20 was fitted to the holder body 10, and both flanges 13, 23 were welded to be sealed by ultrasonic welding. A nozzle (Fuji Clean Tip, Fuji Photo Film Co., Ltd.) was attached as the nozzle for sucking blood to the blood inlet 14 to complete the filter unit.

(3) Collection of Blood 10 ml of vein blood was drawn from a healthy man using a vacuum blood collection tube containing heparin (Terumo). The hematocrit value of the blood was measured and found to be 44%. Each 3 ml of the blood was put in three 4 ml plastic test tubes.

(4) Suction Apparatus

A compact suction apparatus was prepared which was connected to a peristaltic pump of which the exhaust velocity was variable. A suction adapter made of silicone rubber which was connectable to the suction port of the filter unit under airtight conditions was attached to the end of the tube of the compact suction apparatus. A gauge for monitoring pressure was connected to the midway of the tube.

(5) Filtration of Blood

The nozzle for sucking blood of the filter unit was inserted into the blood collected in item (2), and the other end of the filter unit was connected to the suction adapter of the suction apparatus. The exhaust velocity of the suction apparatus was adjusted so that the pressure reduction degree reached 100 mmHg after 30 seconds, and suction was continued. The pressure reduction degree after 10 seconds was 30 mmHg.

(6) Recovery of Plasma

Plasma was streamed into the plasma receiver with the proceeding of suction. The amount of the plasma was 330 µl. The color of the plasma was light yellow, and hemolyzate and contamination of red blood cells were not observed.

(7) Recovery of Filtration Residues

After removing the plasma, the filtration residues accumulated in the blood filtering material was washed twice each with 2 ml saline fed from the blood inlet. Then, the filtration residues were recovered by feeding 2 ml saline from the filtrate outlet. Recovered erythrocytes were observed, and no broken erythrocytes was found. The recovered erythrocytes were hemolyzed, and used as a sample for measuring hemoglobin AIC.

What is claimed is:

1. A method for recovering filtration residues of blood which comprises filtering blood by a blood filtering device comprising a blood filtering material comprising a glass fiber filter having a retainable particle size of 0.6 to 9 µm and having a microporous membrane with a pore size smaller than the retainable particle size of the glass fiber filter and a holder which contains the blood filtering material and has a blood inlet and filtrate outlet, the filtering producing serum or plasma which comes out of the filtrate outlet, and upon finishing the filtering of the blood, feeding an aqueous liquid to the filtrate outlet to the blood filtering material to recover filtration residues accumulated in the blood filtering materials;

wherein the aqueous liquid is selected from the group consisting of pure water, saline and buffers, and the feeding volume is 0.5 to 10 times the volume of the blood filtering material.

2. A method for recovering filtration residues of blood which comprises filtering blood by a blood filtering device comprising a blood filtering material comprising a glass fiber filter having a retainable particle size of 0.6 to 9 µm and having a microporous membrane with a pore size smaller than the retainable particle size of the glass fiber filter and a holder which contains the blood filtering material and has a blood inlet and filtrate outlet, the filtering producing serum or plasma which comes out of the filtrate outlet, and upon finishing the filtering of the blood, feeding an aqueous liquid to the filtrate outlet to the blood filtering material to recover filtration residues accumulated in the blood filtering materials;

wherein the aqueous liquid is selected from the group consisting of pure water, physiological saline, and various buffers.

3. The method of claim 2 wherein the filtering blood is carried out first under a pressure difference between the blood inlet and the filtrate outlet of 50 mmHg or less at least for 5 seconds, and keeping the pressure difference 200 mmHg or less through filtering blood.

* * * * *